United States Patent [19]

Avar et al.

[11] 3,935,231
[45] Jan. 27, 1976

[54] NOVEL BENZOTHIOPHENE DERIVATIVES AS STABILIZERS FOR ORGANIC COMPOUNDS

[75] Inventors: Lajos Avar, Binningen; Kurt Hofer, Munchenstein, both of Switzerland

[73] Assignee: Sandoz Ltd., (Sandoz AG), Basel, Switzerland

[22] Filed: Oct. 11, 1973

[21] Appl. No.: 405,462

[30] Foreign Application Priority Data
Oct. 17, 1972  Switzerland.................... 15187/72

[52] U.S. Cl. ....... 260/330.5; 117/138.5; 117/138.8; 117/141; 117/143 R; 252/404; 260/93.7; 260/94.9 GD
[51] Int. Cl.²..................................... C07D 333/56
[58] Field of Search.................. 260/330.5, 346.2 R

[56] References Cited
UNITED STATES PATENTS

| | | | |
|---|---|---|---|
| 3,180,733 | 4/1965 | Neugebauer et al..................... | 96/33 |
| 3,379,779 | 4/1968 | Strobel et al. ....................... | 260/248 |
| 3,426,124 | 2/1969 | Baron et al. ........................... | 424/59 |
| 3,485,835 | 12/1969 | Brandstrom et al. ............ | 260/247.7 |
| 3,514,465 | 5/1970 | Possett et al........................ | 260/296 |
| 3,558,616 | 1/1971 | Brandstrom et al. ............ | 260/247.1 |

FOREIGN PATENTS OR APPLICATIONS
553,621  6/1957  Belgium........................ 260/346.2

OTHER PUBLICATIONS
Maziere, et al., Bull. Soc. Chim., France, 1963: 1000–1003.
Deltour, et al., Arch. Int. Pharmacodyn, 131:84–106, (1961).

*Primary Examiner*—John D. Randolph
*Attorney, Agent, or Firm*—Gerald D. Sharkin; Richard E. Vila; Joseph J. Borovian

[57] ABSTRACT

The present invention concerns benzothiophene acyl (2) derivatives of the formula,

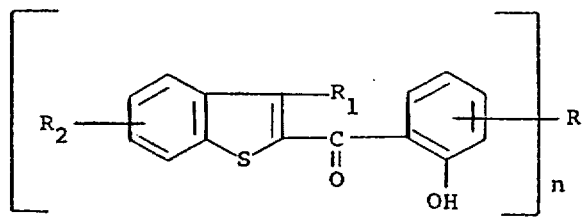

wherein $R_1$, $R_2$ and $R$ are substituents and $n$ is an integer 1 or 2.

The compounds are useful as u.v. stabilizers for, e.g. plastic materials.

8 Claims, No Drawings

NOVEL BENZOTHIOPHENE DERIVATIVES AS STABILIZERS FOR ORGANIC COMPOUNDS

The present invention relates to benzothiophene derivatives and more specifically to benzothiophene acyl (2) derivatives, suitable for stabilizing organic materials against degradation under the influence of ultraviolet radiation, such compounds being hereinafter referred to as U.V. stabilizers.

Accordingly, the present invention provides compounds of formula I,

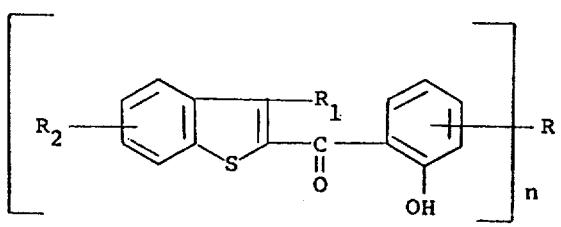

wherein
$R_1$ is hydrogen, halogen or alkyl ($C_1$-$C_8$),
$R_2$ is hydrogen, halogen, alkyl ($C_1$-$C_8$) or alkoxy ($C_1$-$C_8$),
$n$ is an integer 1 or 2,
when
$n$ is 1, R is a monovalent group Rm
wherein
Rm is hydrogen, hydroxy, halogen, alkyl ($C_1$-$C_{12}$), alkoxy ($C_1$-$C_{22}$), 1 alkoxy ($C_1$-$C_8$) mono- or di-oxa-alkoxy ($C_2$-$C_{22}$), ($C_2$-$C_{12}$), thiaalkoxy ($C_2$-$C_{22}$), alkanoyloxyalkoxy ($C_3$-$C_{23}$), alkoxycarbonylalkoxy ($C_3$-$C_{23}$), cyano alkoxy ($C_1$-$C_{22}$), phenyl or a group

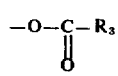

wherein
$R_3$ is alkyl ($C_1$-$C_{21}$), phenyl or phenyl substituted by 1, 2 or 3 members of the group halogen, hydroxy, 1 or 2 alkyls ($C_1$-$C_{22}$) and phenylsulphonyl,
and
when $n$ is 2, R is a divalent group Rd,
wherein
Rd is α,ω-dioxy-alkylene ($C_2$-$C_{12}$),
α,ω-dioxy-thiaalkylene ($C_2$-$C_{12}$),
α,ω-dicarbonyloxyalkylene ($C_4$-$C_{14}$),
α,ω-dicarbonyloxythia-alkylene ($C_4$-$C_{14}$), or a 1,2, a 1,3 or 1,4 dicarbonyloxyphenylene.

It is to be understood that by the term "halogen" as used herein, is meant fluorine, chlorine or bromine, especially chlorine.

When any of $R_1$, $R_2$, $R_3$ and R are or contain an alkyl group, e.g. alkoxy, then the alkyl group may be linear or branched, primary, secondary or tertiary. Examples of primary alkyl groups are the linear alkyl groups methyl, ethyl, n-propyl, n-butyl, n-pentyl and n-hexyl and the branched alkyl groups 2-methyl-1-propyl, 2,2-dimethyl-1-propyl and 2,2-dimethyl-1-butyl. Examples of secondary alkyl groups are isopropyl, 2-butyl, 3-methylbutyl, 2-pentyl, 3-hexyl and 2-methyl-3-pentyl. Examples of tertiary alkyl groups are t-butyl, 2-methyl-2-butyl and t-octyl.

When either $R_1$ or $R_2$ is or contains an alkyl group, then this preferably contains 1 to 6 carbon atoms, more preferably 1 to 5 carbon atoms, especially 1 to 4 carbon atoms.

When R is alkyl, then this preferably contains 1 to 8, more preferably 4 to 8, carbon atoms and most preferably is tertiary alkyl of 4 to 8 carbon atoms, e.g. t-butyl or t-octyl.

When R is alkoxy, then this preferably contains 1 to 18 carbon atoms, for example 1 to 12, 4 to 12 or 4 to 18 carbon atoms.

When $n$ is 2 and R contains an alkylene chain, then this preferably contains 4 to 8, e.g. 4, 5, 6 or 7, carbon atoms.

Examples of R are the monovalent groups
$CH_3O$ $CH_2$ $CH_2$-$O$-
n $C_{12}$ $H_{25}$ $O.OC$ $CH_2$-$O$-
n $C_8$ $H_{17}$ $O.OCC$ $H_2$-$O$-
$C_{11}$ $H_{23}$ $O$ $(CH_2)_8$ -$O$- and
$C_2H_5$ $O.OCCH_2$-$O$-
and the divalent group
$S(CH_2CH_2COO$—$)_2$.

When $R_3$ is alkyl, then this preferably contains 1 to 17 carbon atoms, e.g. 4 to 17 or 8 to 17 carbon atoms.

When $R_3$ is phenyl substituted by alkoxy, then the alkoxy group preferably contains 1 to 8, e.g. 1 to 4 or 1 to 3, carbon atoms.

A preferred group of compounds are the compounds of formula Ia

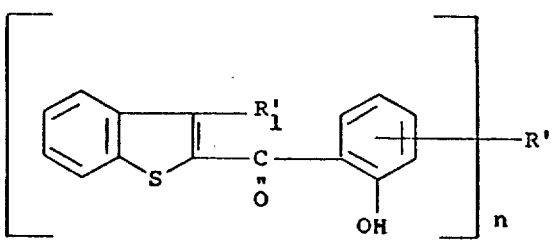

wherein
$n$ is as defined above,
$R'_1$ is hydrogen or halogen and
when
$n$ is 1, R' is a monovalent group Rm'
wherein Rm' is hydroxy, alkoxy ($C_1$-$C_{18}$) or a group

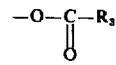

wherein $R_3$ is as defined
above,
and when
$n$ is 2, R' is a divalent group Rd wherein Rd is as defined above.

A further preferred group of compounds are the compounds of formula Ib

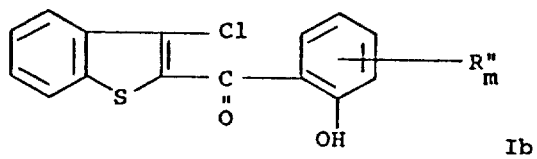

wherein $R''_m$ is hydroxy, alkoxy ($C_1$-$C_{18}$) or a group

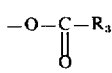

wherein
R₃ is as defined above.
In general, the compounds of formula I wherein $n$ is 1, are the preferred compounds, i.e. the compounds of formula I',

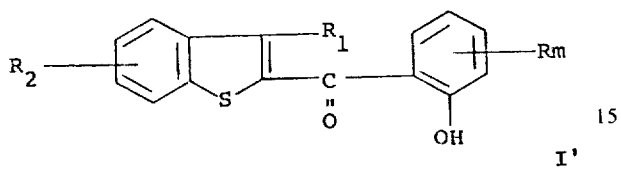

wherein $R_1$, $R_2$ and Rm are as defined above, the compounds of formula Ia',

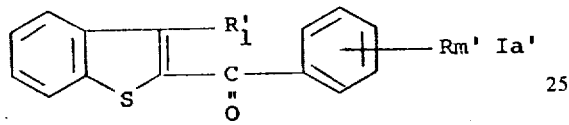

wherein R' and Rm' are as defined above, and the compounds of formula Ib.

A particularly preferred group of compounds of formula I are the compounds of formula Ic,

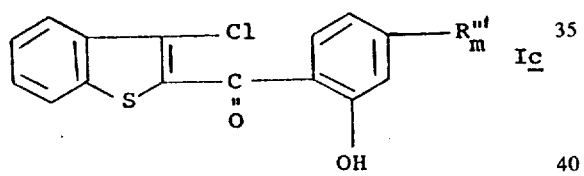

wherein
$R'''_m$ is hydroxy, alkoxy ($C_1$-$C_{12}$), or a group —OOC—R'₃,
wherein
R'₃ is phenyl, phenyl substituted by 1 hydroxy and/or by 1 or 2 alkyls ($C_1$-$C_4$) or phenyl monosubstituted by phenylsulphonyl.

The presentt invention also provides a process for the production of a compound of formula I which comprises
a. hydrolysing or selectively hydrolysing a compound of formula IV,

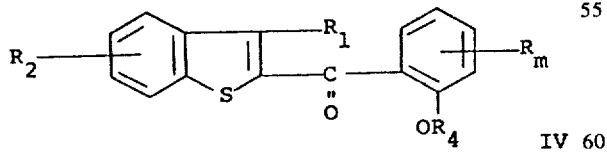

wherein $R_1$, $R_2$ and $R_m$ are as defined above, and $R_4$ is alkyl ($C_1$-$C_{22}$) or aralkyl ($C_7$-$C_{12}$),
to obtain a compound of formula I',
b. selectively mono-esterifying or etherifying a compound of formula I''

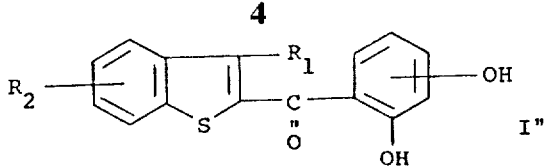

wherein $R_1$ and $R_2$ are as defined above, with a monofunctional compound of formula V, $R_5 — X'$    V wherein $R_5$ is alkyl ($C_1$-$C_{22}$), mono- or dioxa-alkyl ($C_2$-$C_{22}$), thia-alkyl ($C_2$-$C_{22}$), alkanoyloxyalkyl ($C_3$-$C_{23}$), alkoxycarbonylalkyl ($C_3$-$C_{23}$), cyano alkyl ($C_1$-$C_{22}$), phenyl or a group

wherein $R_3$ is as defined above, and X' is a leaving group, preferably halogen, particularly chlorine, or a bifunctional compound of formula VI, $X'' — R_6 — X''$    VI wherein $R_6$ is alkylene ($C_2$-$C_{12}$), thia-alkylene ($C_2$-$C_{12}$) α,ω-dicarbonyl alkylene ($C_4$-$C_{14}$), α,ω-dicarbonyl-thia-alkylene ($C_4$-$C_{14}$), or a 1,2-, a 1,3- or a 1,4-dicarbonylphenylene, and
each or both X'' s is or together form a leaving group, to produce a compound of formula I''',

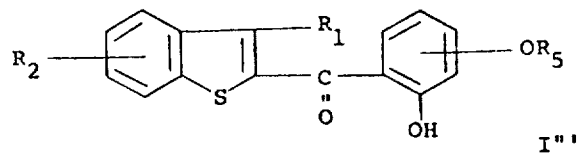

or to produce a compound of formula I^iv,

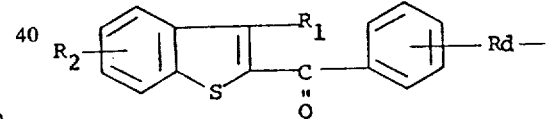

wherein $R_1$, $R_2$ and Rd are as defined above, respectively, or
c. condensing a compound of formula II,

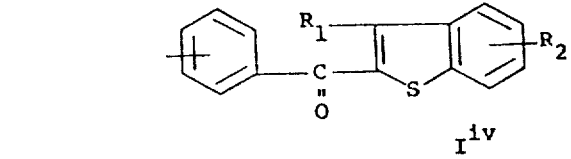

wherein $R_1$ and $R_2$ are as defined above, and Hal is chlorine or bromine,
with a compound of formula VII

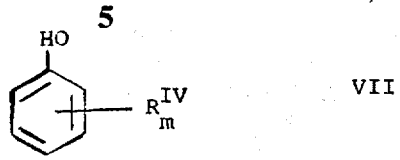

wherein $R_m^{IV}$ is hydrogen, hydroxy, halogen, alkyl ($C_1$-$C_{12}$), alkoxy ($C_1$-$C_{22}$) or phenyl, in the presence of a Friedel-Craft catalyst, to obtain a compound of formula $I^r$,

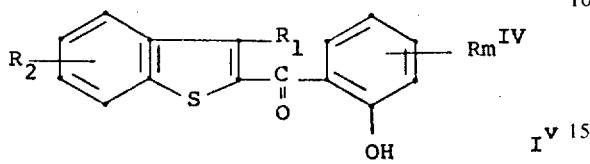

wherein $R_1$, $R_2$ and $Rm^{IV}$ are as defined above.

The process of the invention in accordance with variant (a) may be effected as follows, viz.

The hydrolysis of the compounds of formula IV may be effected by the addition of water or aqueous acid solution and heating the resulting mixture to within a temperature range such as 60° to 100°C, e.g. to 90°C.

Working up is effected in conventional manner.

The process of the invention in accordance with variant (b) may be effected as follows, viz.

The reaction is preferably effected in an inert solvent, e.g. an halogenated hydrocarbon such as chlorobenzene, and conveniently at an elevated temperature, e.g. between 40° and 100°C.

As regards the esterification reaction, the reaction is preferably effected in the presence of an esterification catalyst, e.g. an acid catalyst such as HCl.

As regards the etherification reaction, the reaction is preferably effected in the presence of a basic catalyst, for example triethylamine.

Working up is effected in conventional manner.

Preferably, compounds of formula VIa, $$X''' - R_s - X'''$$ VIa wherein
each $X'''$ is chlorine or bromine or
both $X'''$'s together from an —O— bridge of an acid anhydride functional group, and
$R_s$ is as defined above, with the proviso that when both $X'''$'s together form an —O— bridge, then $R_5$ contains terminal carbonyl groups, are employed as starting materials of formula VI in process variant (b). Examples of such starting materials are 1,8-octylene dibromide, 1,6-hexylene dibromide, aliphatic dicarboxylic acid derivatives, e.g. malonic acid, succinic acid, glutaric acid, adipic acid and sebacic acid derivatives and aromatic dicarboxylic acid derivatives such as 1,2, 1,3 or 1,4 phenylene dicarboxylic acid derivatives.

The reaction may be effected under FriedelCraft conditions as described, for example, in the Journal of Heterocyclic Chemistry, No. 8 (1971) 5, p 711–714.

As Friedel-Craft catalyst, preferably anhydrous aluminium chloride is employed. As the compound of formula II, preferably the acid chloride is employed. Preferably, the reaction is effected in an inert solvent such as an halogenated hydrocarbon, e.g. chlorobenzene. It is advisable to effect the reaction at a temperature below room temperature, e.g. below 0°C such as —10° to 0°C.

Working up is effected in conventional manner.

The compounds of formula I are useful as u.v. stabilizers, i.e. they protect sensitive organic material from degradation under the effect of U.V. light, as indicated in the following test, viz.

Test

Unstabilized polypropylene, in powder form, is homogeneously mixed with 0,5 % by weight of a compound of formula I e.g.

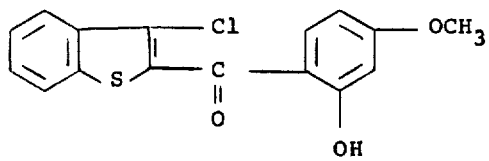

and the mixture kneaded for 5 minutes on a roller mill at 180°C. The kneaded mixture is then pressed into sheets of 0,3 mm thickness.

The relative stability to U.V. radication of the sheet so produced is determined by the De la Rue method in the climate test at 40°C and 75 % relative air humidity employing 16 sun lamps and 16 black lamps (supplied by the firm Philips) and insuring good ventilation. The test is repeated with an untreated control sheet and the results compared. More damage in the untreated sheet indicates a U.V. stabilizing action on the part of the compound employed in the test.

The test was repeated employing polyethylene and a compound of formula I e.g.

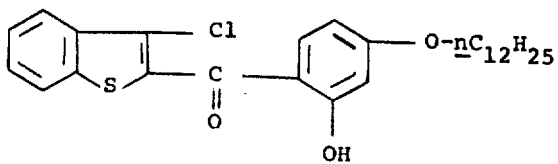

The compounds of formula I are useful for the stabilization of organic material, particularly plastics material, susceptible to U.V. degradation, by a method which comprises treating the organic material with a compound of formula I.

It is to be understood that by the term "treating" is meant either surface coating the organic material with the compound of formula I, in the form of a film, or incorporating the compound of formula I into the body of the organic material, preferably the latter, in manner known per se.

The above method also forms part of the present invention. Thus, according to a first embodiment, the method may be effected by intimately mixing the U.V. stabilizer with a particulate form of, for example, a plastic material, such as polypropylene, e.g. polypropylene granules, in a kneader or other suitable device, to obtain uniform distribution of the antioxidant throughout the plastic material. The plastics material may thereafter be formed into final shape, e.g. by extrusion or injection moulding. By such method, uniform distribution of the antioxidant throughout the body of the final material is achieved which is important for good protection.

According to a second embodiment, organic material in final form, for example, a textile filament, is passed through a dispersion of the antioxidant, e.g. in aqueous medium, to provide a protective coating of the U.V.

stabilizer as a surface film on the organic material. Textile filaments or fabrics of polyethylene terephthalate or cellulose acetate are suited to this mode of application.

According to a third embodiment of the method of the present invention, particularly suited to stabilization of polymers or copolymers susceptible to degradation by reaction of U.V. light, e.g. polypropylene, the U.V. stabilizer is mixed with the monomer or prepolymer before polymerisation or, as the case may be, copolymerisation, is effected, to yield the polymer or copolymer having the U.V. stabilizer uniformly distributed therethrough. The polymer or copolymer may thereafter be extruded, moulded or otherwise formed into final shape.

Examples of organic materials susceptible to U.V. degradation and embraced by the method of the present invention, are cellulose derivatives, e.g. cellulose acetate, cellulose acetobutyrate, ethyl cellulose, cellulose nitrate and cellulose propionate, polyalkylenes, e.g. polyethylene and polypropylene, polyvinyl derivatives, e.g. polyvinyl chloride, polyvinyl chloride acetate and polyvinyl alcohol, polyamides, polyesters, polyacrylonitrile, polystyrene, silicon rubber, melamineformaldehyde resins, ureaformaldehyde resins, alkyl casting resins, polymethylacrylate, copolymers such as acrylonitrile - butadiene - styrene copolymers and natural products such as rubber, cellulose, wool and silk.

Stabilized organic materials according to the invention may exist in solid form, e.g. solid forms such as form plastics, panels, rods, coating, sheets such as paper, film tapes, fibres, granules or powders, or in liquid form, e.g. solutions, emulsions or dispersions such as polishes, paints and creams.

The organic material may also be treated with other additives, e.g. antioxidants, heat and U.V. stabilizers. Other additives that may be mentioned are 2-hydroxybenzophenones, 1,2,3-triazoles, tin and trivalent phosphorus organic compounds and nickel salts of carboxylic acids.

The amount of U.V. stabilizer employed in the method of the present invention will, of course, vary with the mode of application, the compound employed and the nature of the organic material to be treated.

Thus, for example, when the mode of application is the uniform distribution of the U.V. stabilizer throughout the body of the organic material, then in general, satisfactory results are obtained when the amount of U.V. stabilizer employed is between 0,01 and 5 %, preferably between 0,05 and 1 % of the weight of organic material to be treated.

Examples of the process of the invention will now be described. Where temperatures are referred to, these are in °C. Where parts and percentages are referred to, these are by weight.

EXAMPLE 1:

42.8 Parts of resorcinol dimethyl ether and 76.6 parts of 3-chloro benzenethiophencarboxylic acid chloride-(2) are dissolved in 500 parts of chlorobenzene. The temperature is kept to −9° to 0°C, with stirring, and 41.3 parts of anhydrous aluminium chloride are added in portions over 1½ hours. After the splitting off of the theoretical amount of HCl, the mixture is heated to 90°C in order to complete the ether splitting. Subsequently, HCl-ice water is added to the mixture, the organic phase is separated, washed neutral, the solvent is distilled off and the residue is crystallised from ethanol/dioxan; the compound

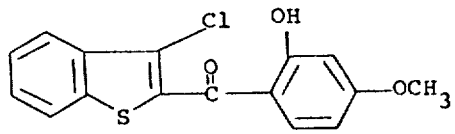

of m.p. 122°–124°C is obtained.

| Elementary analysis | C | H | Cl | S |
|---|---|---|---|---|
| Calc. : | 60.2% | 3.4% | 11.1% | 10.0% |
| Found : | 60.4% | 3.6% | 11.3% | 9.9% |

In analogous manner, the compounds of the following Examples listed in the following Table 1 are also obtained.

TABLE 1

| Example No. | R | m.p. °C |
|---|---|---|
| 2 | —OH | 197–200 |
| 3 | —O—nC₁₉H₂₅ | 40–42 |
| 4 | —O—C(=O)—nC₁₇H₃₅ | 68–69 |
| 5 | —O—C(=O)—C₆H₄—SO₂—C₆H₅ | 154–158 |
| 6 | —O—C(=O)—C₆H₂(+)₂—OH | 96–100 |

N.B. + denotes —C(CH₃)₃

EXAMPLE 7:

6.08 Parts of the compound of Example 2 (Table 1) are dissolved in 200 ml of toluene and 3 parts of triethylamine added. The mixture is heated to 80° and 2 parts of terephthalic acid chloride, at the same temperature, are added with stirring. The reaction mixture is stirred for 1 hour at 80° and then the reaction mixture is heated for a further 3 hours at the boiling temperature under reflux. The reaction mixture is then allowed to cool, is washed with water at 60°, and the toluene phase separated in a separating funnel. The toluene is evaporated off and the residue taken up and crystallised from dioxan/methanol.

The compound

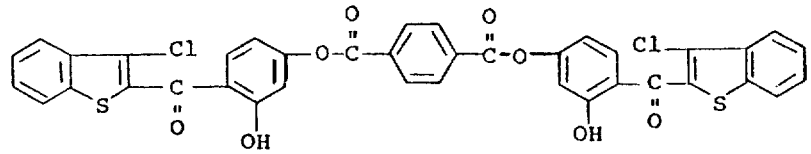

is obtained.

1. A compound of the formula

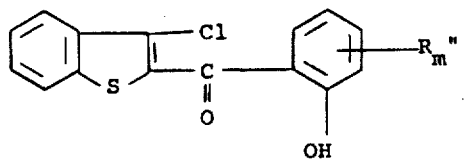

wherein $R_m''$ is hydroxy, alkoxy ($C_1$-$C_{18}$), or a group

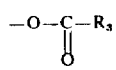

wherein $R_3$ is alkyl ($C_1$-$C_{21}$), phenyl or phenyl substituted by 1, 2 or 3 members of the group halo, hydroxy, 1 or 2 alkyls ($C_1$-$C_{22}$), 1 alkoxy ($C_1$-$C_8$) and phenylsulphonyl.

2. A compound of claim 1 of the formula

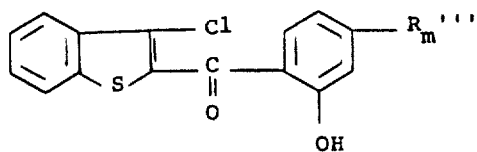

wherein
$R_m'''$ is hydroxy, alkoxy($C_1$-$C_{12}$), or a group —OO-C—$R_3'$,
wherein
$R_3'$ is phenyl, phenyl monosubstituted by hydroxy, phenyl monosubstituted by hydroxy and mono- or di-substituted by alkyl($C_1$-$C_4$), phenyl mono- or di-substituted by alkyl($C_1$-$C_4$) or phenyl monosubstituted by phenylsulphonyl.

3. The compound of claim 2 of the formula

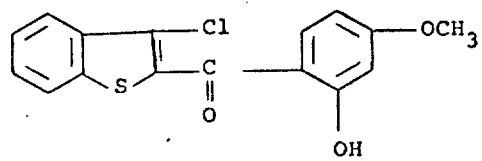

4. The compound of claim 2 of the formula

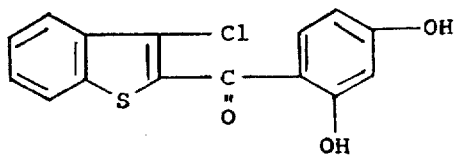

5. The compound of claim 2 of the formula

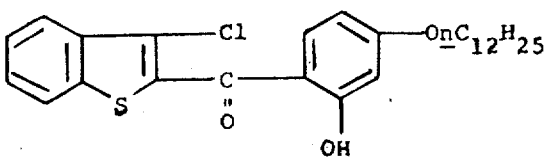

6. The compound of claim 1 of the formula

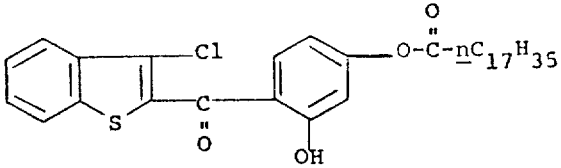

7. The compound of claim 2 of the formula

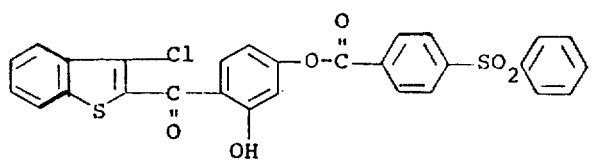

8. The compound of claim 2 of the formula

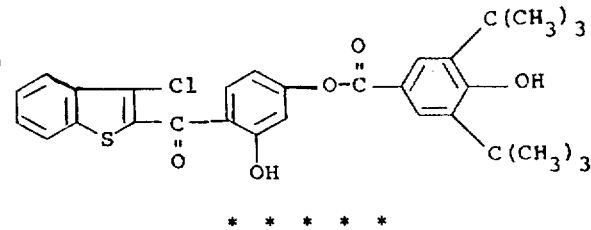

* * * * *